United States Patent
Fedurco et al.

(10) Patent No.: US 11,155,540 B2
(45) Date of Patent: Oct. 26, 2021

(54) SULFURIZED BENZOXAZINE FOR USE IN THE SYNTHESIS OF A POLYBENZOXAZINE

(71) Applicant: COMPAGNIE GENERALE DES ETABLISSEMENTS MICHELIN, Clermont-Ferrand (FR)

(72) Inventors: Milan Fedurco, Clermont-Ferrand (FR); Marco Ribezzo, Clermont-Ferrand (FR)

(73) Assignee: COMPAGNIE GENERALE DES ETABLISSEMENTS MICHELIN, Clermont-Ferrand (FR)

( * ) Notice: Subject to any disclaimer, the term of this patent is extended or adjusted under 35 U.S.C. 154(b) by 47 days.

(21) Appl. No.: 16/621,497

(22) PCT Filed: Jun. 12, 2018

(86) PCT No.: PCT/FR2018/051367
§ 371 (c)(1),
(2) Date: Dec. 11, 2019

(87) PCT Pub. No.: WO2018/229415
PCT Pub. Date: Dec. 20, 2018

(65) Prior Publication Data
US 2020/0199112 A1    Jun. 25, 2020

(30) Foreign Application Priority Data
Jun. 14, 2017    (FR) .................... 1755350

(51) Int. Cl.
*C07D 413/10* (2006.01)
*C08G 73/02* (2006.01)
*C09J 179/04* (2006.01)

(52) U.S. Cl.
CPC ....... *C07D 413/10* (2013.01); *C08G 73/0233* (2013.01); *C09J 179/04* (2013.01)

(58) Field of Classification Search
CPC ............... C07D 413/10; C08G 73/0233
USPC ....................................................... 544/90
See application file for complete search history.

(56) References Cited

U.S. PATENT DOCUMENTS

| | | | |
|---|---|---|---|
| 5,543,516 A | 8/1996 | Ishida | |
| 9,617,372 B2 | 4/2017 | Fedurco et al. | |
| 9,840,644 B2 | 12/2017 | Doisneau et al. | |
| 9,845,376 B2 | 12/2017 | Fedurco et al. | |
| 10,005,929 B2 | 6/2018 | Doisneau et al. | |
| 10,040,976 B2 | 8/2018 | Doisneau et al. | |
| 10,150,833 B2 | 12/2018 | Fedurco et al. | |
| 10,800,795 B2 | 10/2020 | Fedurco et al. | |
| 10,975,044 B2 | 4/2021 | Fedurco et al. | |
| 10,995,076 B2 | 5/2021 | Fedurco et al. | |
| 2014/0235124 A1 | 8/2014 | Doisneau et al. | |
| 2014/0235125 A1 | 8/2014 | Doisneau et al. | |
| 2014/0308864 A1 | 10/2014 | Doisneau et al. | |
| 2015/0259463 A1 | 9/2015 | Fedurco et al. | |
| 2015/0274878 A1 | 10/2015 | Fedurco et al. | |
| 2016/0122460 A1 | 5/2016 | Fedurco et al. | |
| 2016/0251550 A1 | 9/2016 | Michoud et al. | |
| 2018/0118983 A1 | 5/2018 | Doisneau et al. | |
| 2018/0370284 A1 | 12/2018 | Fedurco et al. | |
| 2019/0300765 A1 | 10/2019 | Fedurco et al. | |
| 2020/0095458 A1 | 3/2020 | Fedurco et al. | |
| 2020/0208010 A1 | 7/2020 | Fedurco et al. | |
| 2020/0290402 A1 | 9/2020 | Fedurco et al. | |
| 2021/0146725 A1 | 5/2021 | Fedurco et al. | |

FOREIGN PATENT DOCUMENTS

| | | |
|---|---|---|
| JP | 2010-265480 A | 11/2010 |
| WO | 2013/017421 A1 | 2/2013 |
| WO | 2013/017422 A1 | 2/2013 |
| WO | 2013/017423 A1 | 2/2013 |
| WO | 2013/148408 A1 | 10/2013 |

(Continued)

OTHER PUBLICATIONS

Poorteman Marc et al. Progress in Organic Coatings, vol. 97, 2016, pp. 99-109.*
International Search Report dated Aug. 1, 2018, in corresponding PCT/FR2018/051367 (4 pages).
M. Poorteman, et al., "Thermal curing of para-phenylenediamine benzoxazine for barrier coating applications on 1050 aluminum alloys", Progress in Organic Coatings, Elsevier BV, NL, vol. 97, pp. 99-109 (2016) XP029557542.

(Continued)

*Primary Examiner* — Kahsay Habte
(74) *Attorney, Agent, or Firm* — Venable LLP

(57) ABSTRACT

A sulfurized benzoxazine compound, which is usable for the synthesis of a polybenzoxazin, corresponds to formula (A):

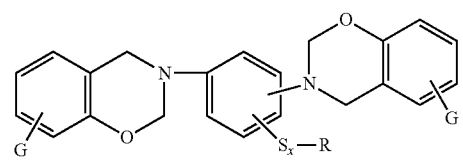

Figure 1A:
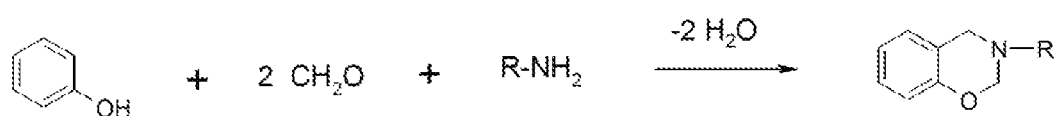

in which: each benzene nucleus of the two oxazine rings bears at least one radical denoted as "G"; the two oxazine rings are connected together via a central aromatic group, the benzene ring of which bears one, two, three or four groups of formula —$S_x$—R in which "x" is an integer from 1 to 8 and R represents hydrogen or a hydrocarbon-based group including 1 to 10 carbon atoms and optionally a heteroatom chosen from O, S, N and P; and the at least two radicals G, which may be identical or different, are chosen from various groups.

20 Claims, 11 Drawing Sheets

(56) References Cited

FOREIGN PATENT DOCUMENTS

| WO | 2014/063963 A1 | 5/2014 |
| WO | 2014/063968 A1 | 5/2014 |
| WO | 2014/173838 A1 | 10/2014 |
| WO | 2014/173839 A1 | 10/2014 |
| WO | 2015/007641 A1 | 1/2015 |
| WO | 2015/007642 A1 | 1/2015 |

OTHER PUBLICATIONS

N.N. Ghosh, et al., "Polybenzoxazines—New high performance thermosetting resins: Synthesis and properties", Prog. Polym. Sci. 32 (2007) 1344-1391.

Y. Yagci, et al., "Recent Advancement on Polybenzoxazine—A Newly Developed High Performance Thermoset", J. Polym. Sci. Part A: Polym. Chem., vol. 47 (2009) 5565-5576.

* cited by examiner

Monomer M-0

Monomer M-1

Monomer M-2

Monomer M-3

(A-4)

Monomer M-4

(A-5)

Monomer M-5

↓ Δ

(II-2)

Polymer P-2'

SULFURIZED BENZOXAZINE FOR USE IN THE SYNTHESIS OF A POLYBENZOXAZINE

1. FIELD OF THE INVENTION

The present invention relates to monomers that may be used for the synthesis of thermosetting resins, intended especially for adhesive systems in particular allowing the adhesive bonding of metal to rubber.

The invention relates more particularly to benzoxazine compounds suitable for the synthesis of polybenzoxazines that may be used in particular as adhesive layers in metal/rubber composites intended for the manufacture of rubber articles such as pneumatic or non-pneumatic tyres, for vehicles.

2. PRIOR ART

Metal/rubber composites, in particular for motor vehicle tyres, are well known. They are usually composed of a matrix made of unsaturated rubber, generally diene rubber, which can be crosslinked with sulfur, including metal reinforcing elements (or "reinforcers") such as yarns, films, tapes or cords made of carbon steel.

As they are subjected to very high stresses during the rolling of the tyres, notably to repeated actions of compression, bending or variations in curvature, these composites must, in a known manner, satisfy a large number of sometimes contradictory technical criteria, such as uniformity, flexibility, flexural strength and compressive strength, tensile strength, wear resistance and corrosion resistance, and must maintain these performance qualities at a very high level for as long as possible.

It is easily understood that the adhesive interphase between rubber and reinforcers plays a predominant role in the endurance of these performance qualities. The conventional process for connecting rubber compositions to carbon steel consists in coating the surface of the steel with brass (copper/zinc alloy), the bonding between the steel and the rubber matrix being provided by sulfurization of the brass during the vulcanization or curing of the rubber. In order to improve the adhesion, use is generally made, in addition, in these rubber compositions, of organic salts or metal complexes, such as cobalt salts, as adhesion-promoting additives.

However, it is known that the adhesion between the carbon steel and the rubber matrix is liable to weaken over time as a result of the gradual development of the sulfides formed, under the effect of the various stresses encountered, notably mechanical and/or thermal stresses, it being possible for the above degradation process to be accelerated in the presence of moisture. Moreover, the use of cobalt salts renders the rubber compositions more sensitive to oxidation and to ageing, and significantly increases the cost thereof, not to mention that it is desirable to eliminate, in the long run, the use of such cobalt salts in rubber compositions due to the recent change in European regulations relating to metal salts of this type.

For all the reasons set out above, manufacturers of metal/rubber composites, in particular motor vehicle tyre manufacturers, are seeking novel adhesive solutions in order to adhesively bond metal reinforcers to rubber compositions, while overcoming, at least in part, the abovementioned drawbacks.

Thus, the recently published patent applications WO 2014/063963, WO 2014/063968, WO 2014/173838 and WO 2014/173839, filed by the Applicant Companies, have described novel polymers bearing urea, urethane or thiourea units, and also their starting monomers, which meet the above objectives. Used notably as adhesion primer on metal in metal/rubber composites, these polymers make it possible very advantageously to adhesively bond the metal to the rubber matrices by subsequently using simple textile adhesives, such as "RFL" (resorcinol/formaldehyde latex) adhesives or other equivalent adhesive compositions, or else directly (that is to say, without employing such adhesives) to these rubber matrices when the latter contain, for example, appropriate functionalized unsaturated elastomers, such as epoxidized elastomers. Thus, the cobalt salts (or other metal salts) can notably be left out of the rubber compositions intended to be connected to brass-coated metal reinforcers.

In continuing their research, the Applicant Companies have found a novel benzoxazine compound, that may be used as a monomer for the synthesis of a polybenzoxazine, of thermosetting type, which at room temperature has the same adhesive performance, with respect to metal and rubber, as the abovementioned polymers, but which has, once thermoset (crosslinked), further improved thermal and chemical stability and the specific microstructure thereof moreover makes it possible very advantageously to adjust the flexibility of the molecule depending on the particular applications targeted.

3. SUMMARY OF THE INVENTION

The present invention relates to a sulfurized benzoxazine corresponding to formula (A):

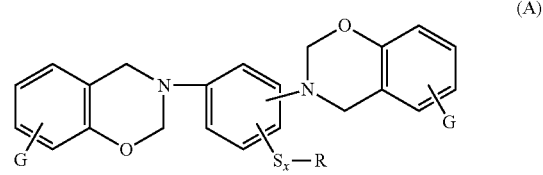

(A)

in which:
each benzene nucleus of the two oxazine rings bears at least one radical denoted as "G";
the two oxazine rings are connected together via a central aromatic group, the benzene ring of which bears one, two, three or four groups of formula —$S_x$—R in which "x" is an integer from 1 to 8 and R represents hydrogen or a hydrocarbon-based group including 1 to 10 carbon atoms and optionally a heteroatom chosen from O, S, N and P;
the at least two radicals G, which may be identical or different, are chosen from the group consisting of:
halogens;
groups —$OR_1$, —$SR_1$, —$NR_2R_3$; $R_1$, $R_2$ and $R_3$, which may be identical or different, representing an alkyl containing 1 to 4 carbon atoms; and
aliphatic hydrocarbon-based groups including 1 to 8 carbon atoms, or cycloaliphatic hydrocarbon-based groups including 3 to 8 carbon atoms, or aromatic hydrocarbon-based groups including 6 to 12 carbon atoms, these saturated or ethylenically unsaturated hydrocarbon-based groups also optionally including at least one heteroatom chosen from O, S, N and P.

By means of this specific benzoxazine, it is possible to prepare benzoxazine polymers or "polybenzoxazines" which have the noteworthy capacity, at high temperature, of opening their oxazine rings and thus of leading to a thermosetting polyphenolic resin structure. This gives them, when compared with the other known polymers described in the introduction of the present specification, better thermal stability. Its specific microstructure makes it possible, finally, very advantageously, to adjust the flexibility of the polybenzoxazines according to the particular targeted applications.

The invention also relates to the use of a compound in accordance with the invention for the synthesis of a polybenzoxazine, and also to any polybenzoxazine derived from at least one benzoxazine compound according to the invention.

The invention also relates to any process for synthesizing a polybenzoxazine by polycondensation of a compound according to the invention, notably with, as second monomer, an aromatic diol or thiol compound.

4. BRIEF DESCRIPTION OF THE FIGURES

Figure 1B:
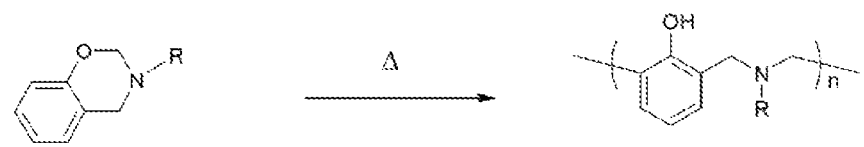
Figure 2:
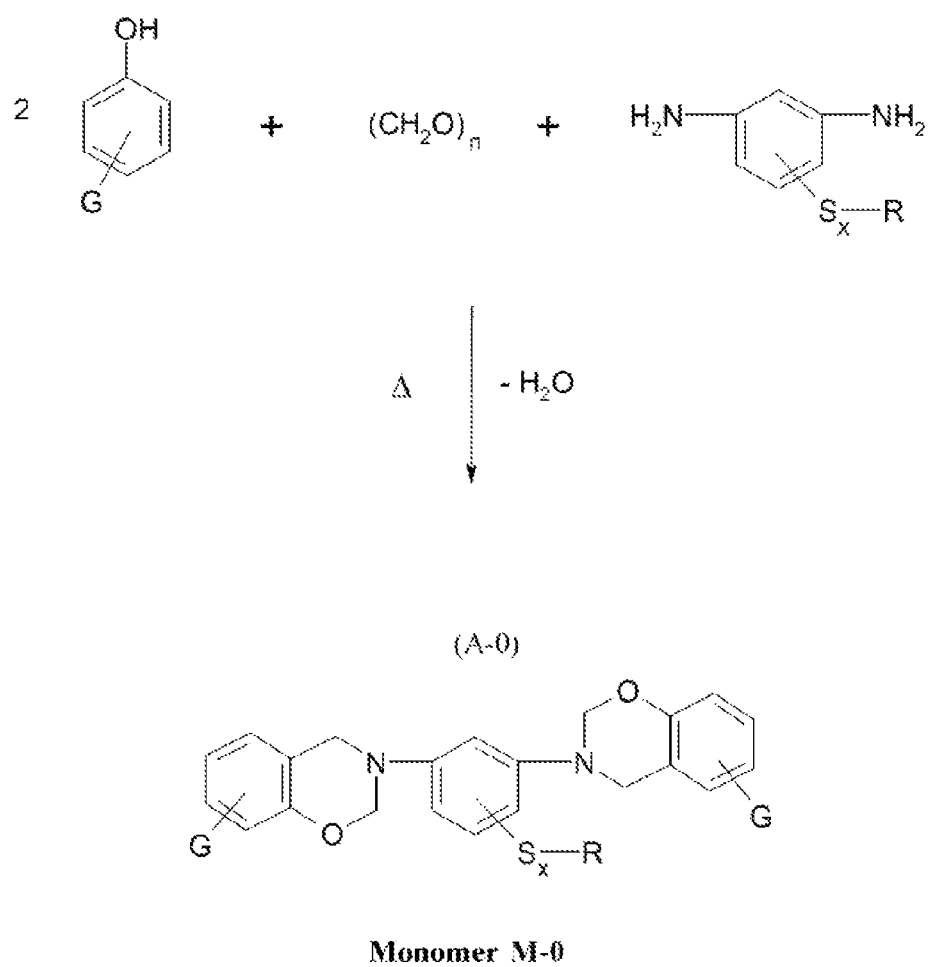
Figure 3:
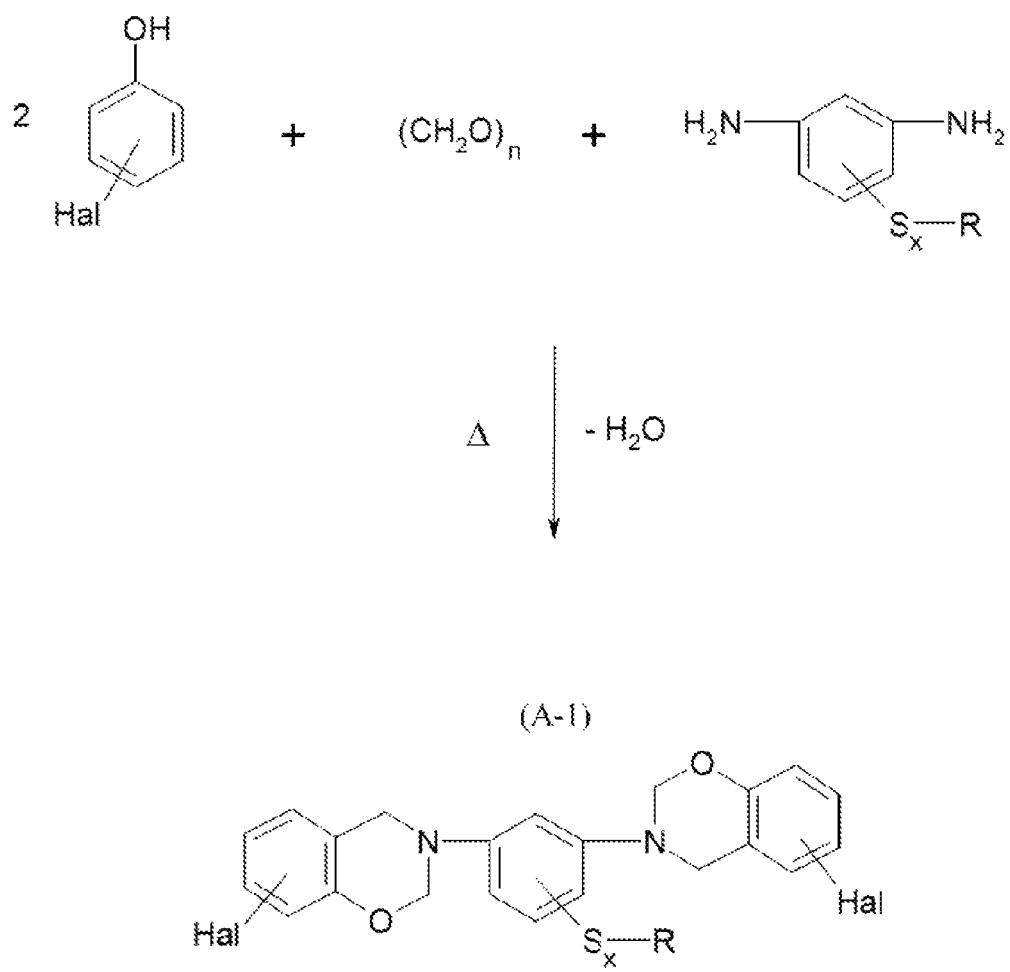
Figure 4:
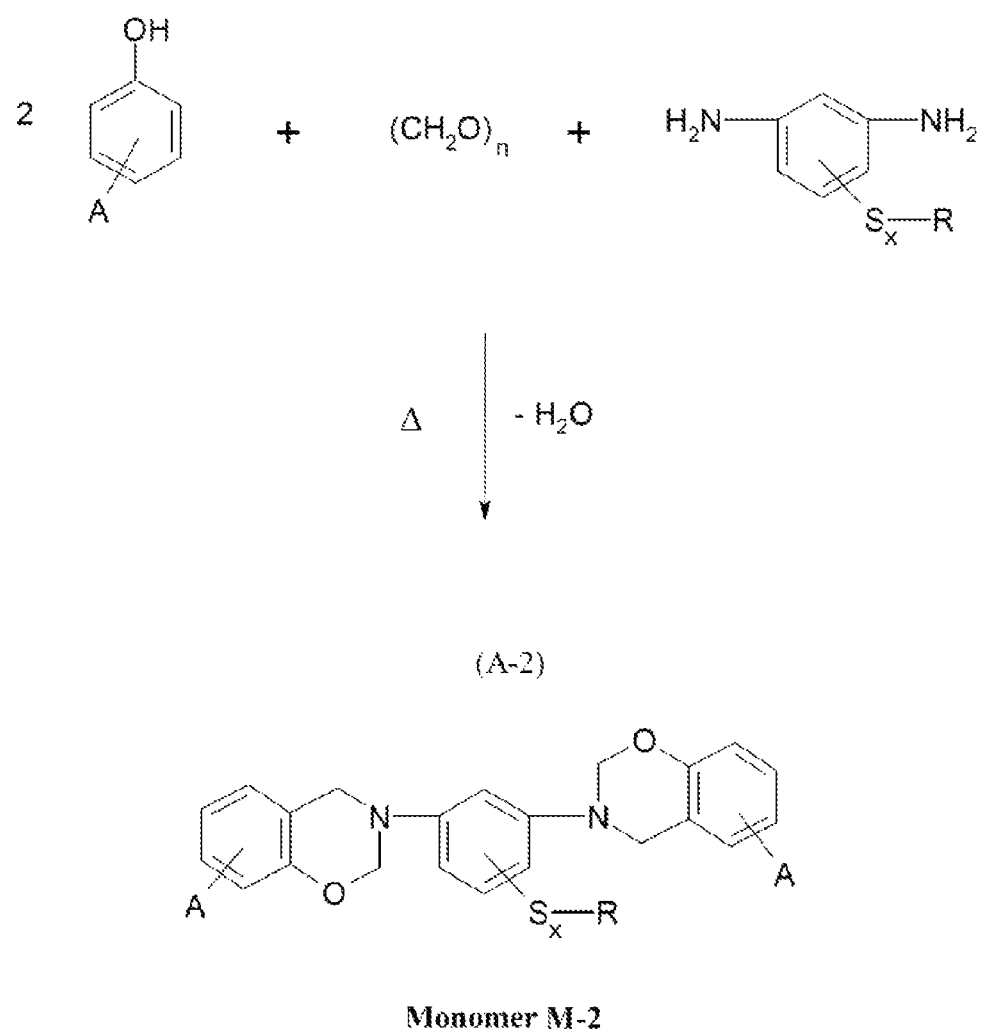
Figure 5:
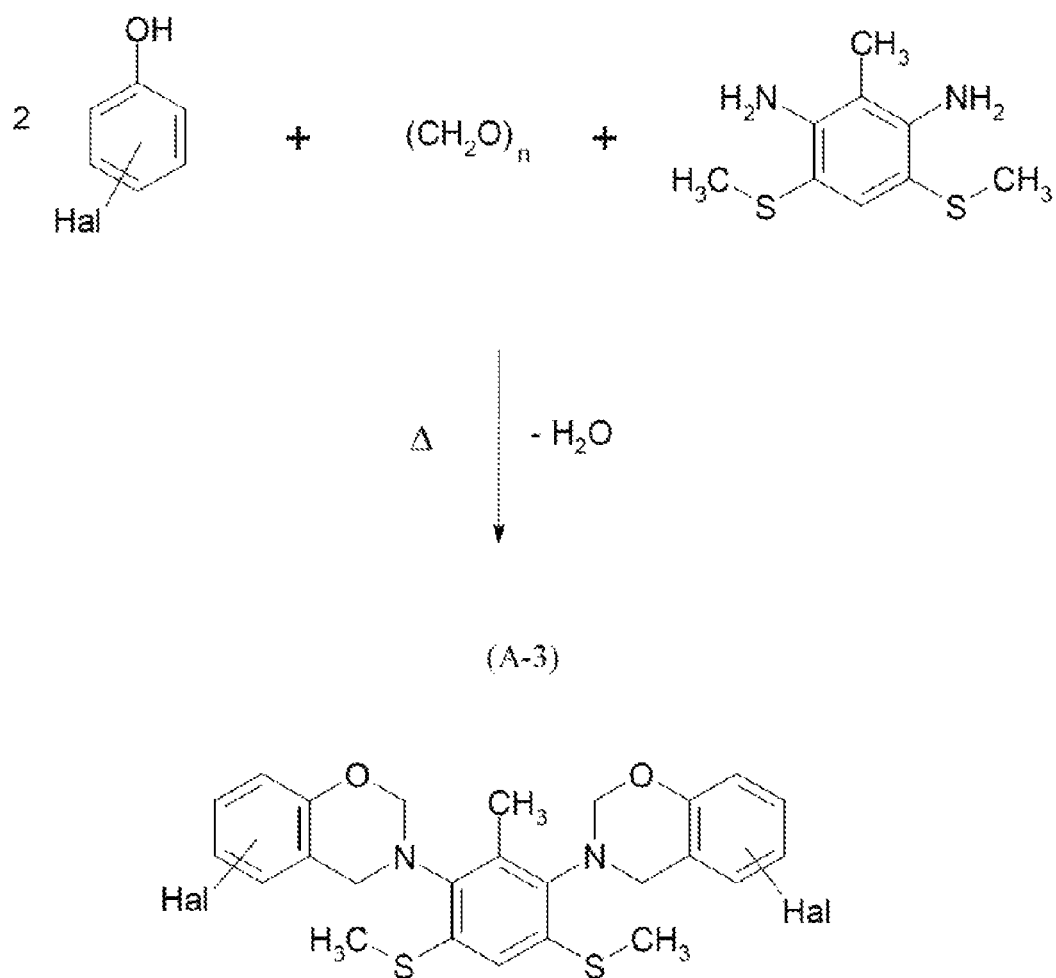
Figure 6:
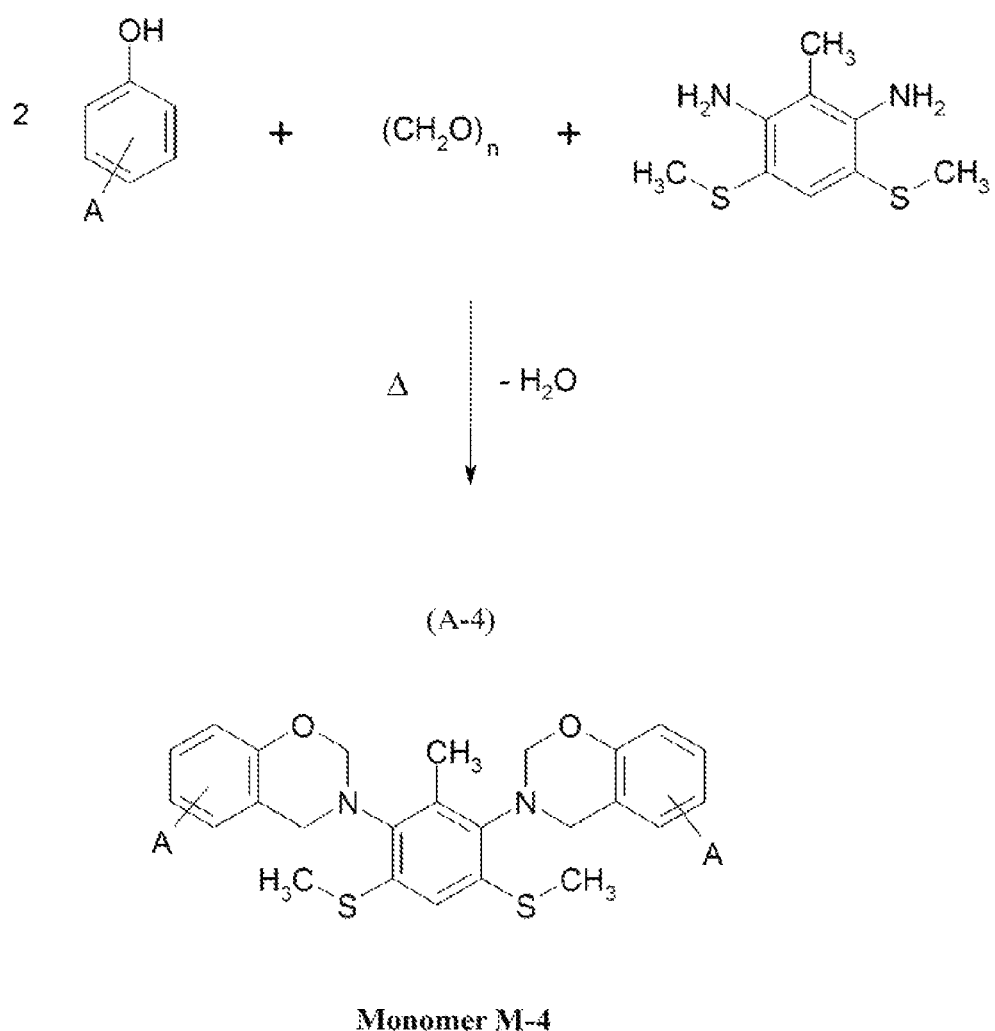
Figure 7:
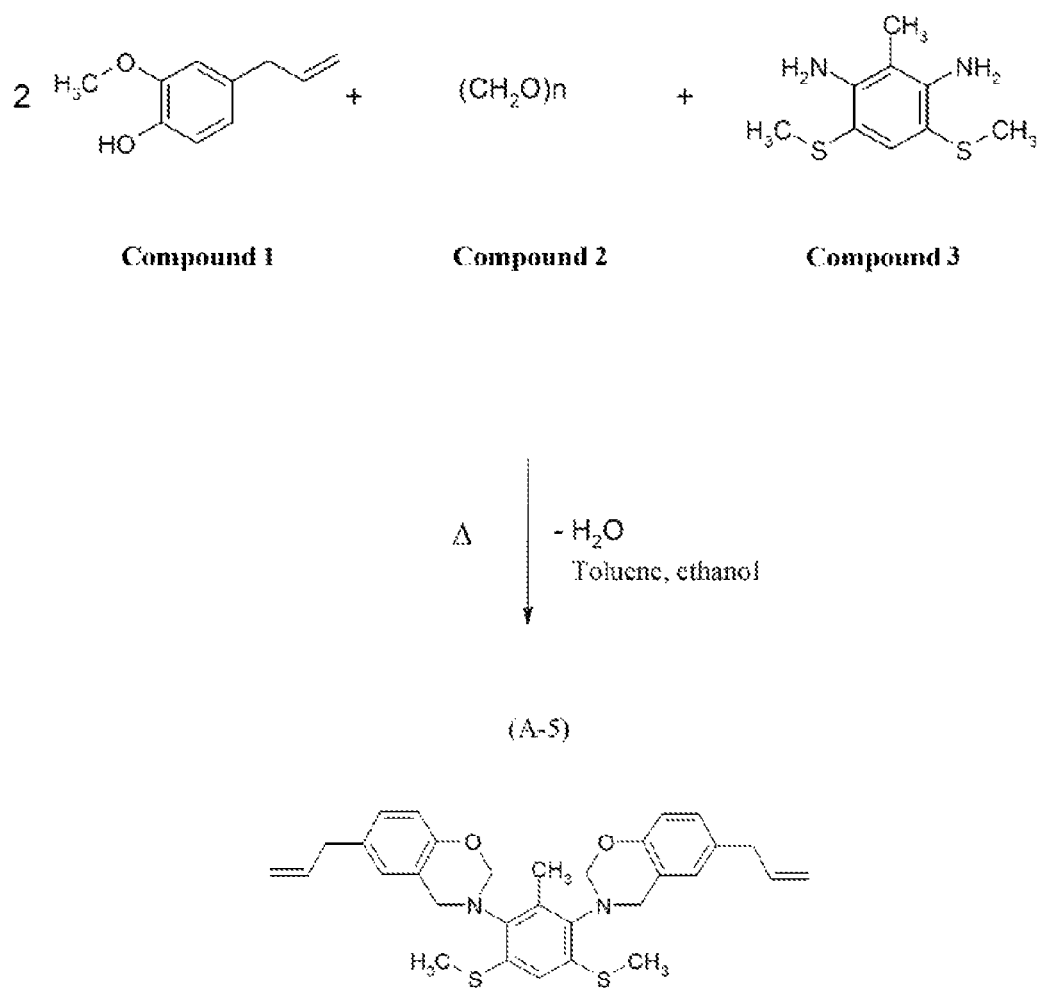
Figure 8:
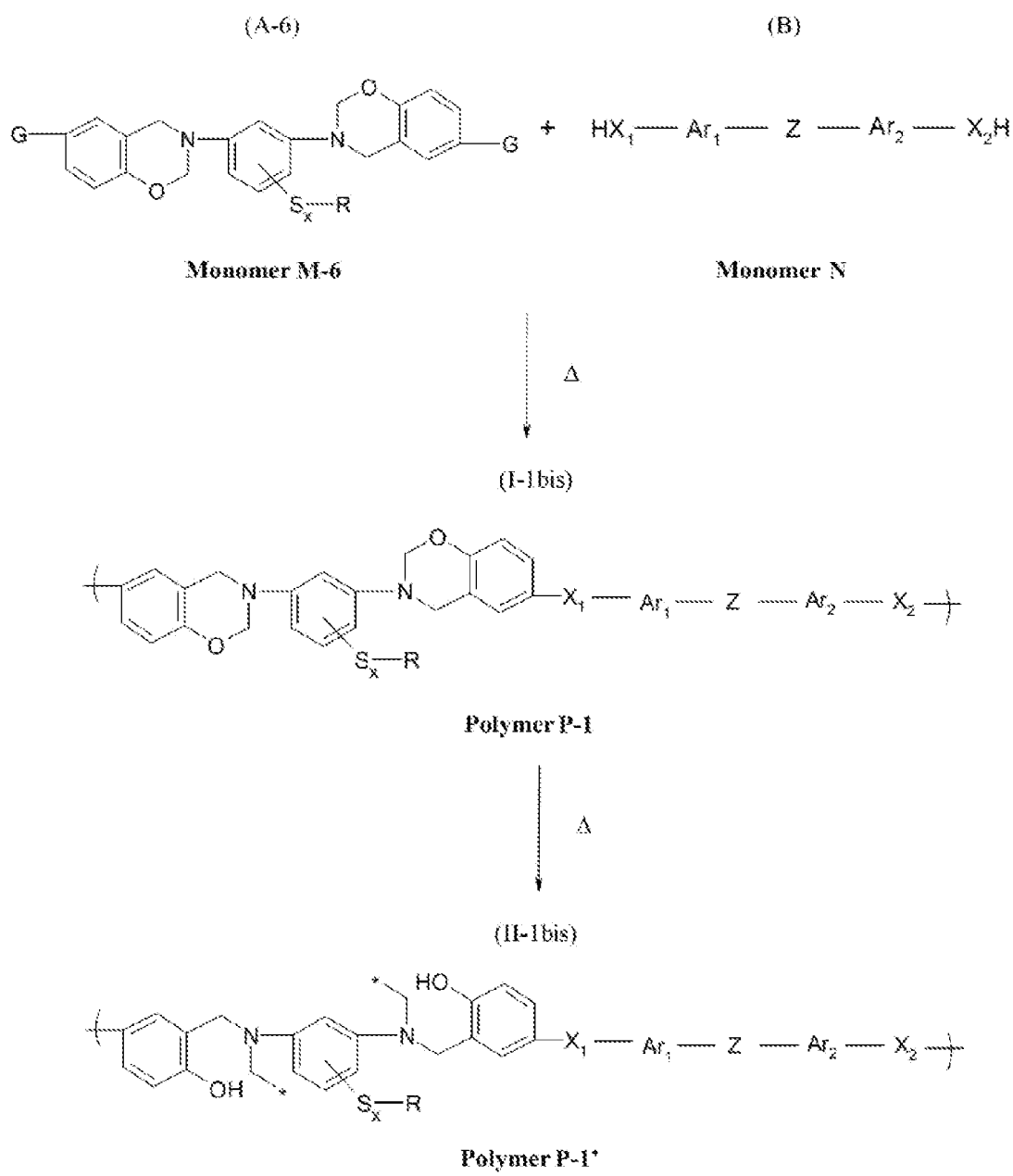
Figure 9:
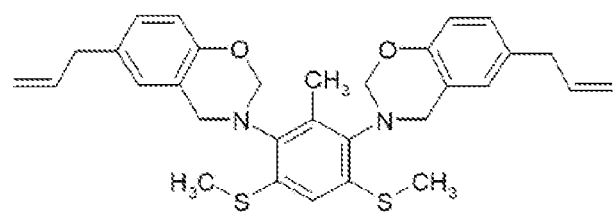
Figure 9:
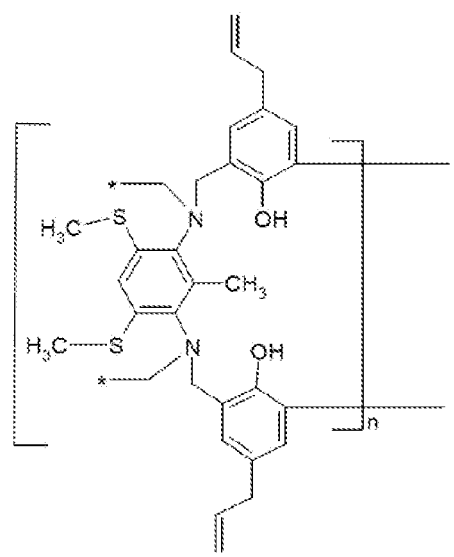
Figure 10:
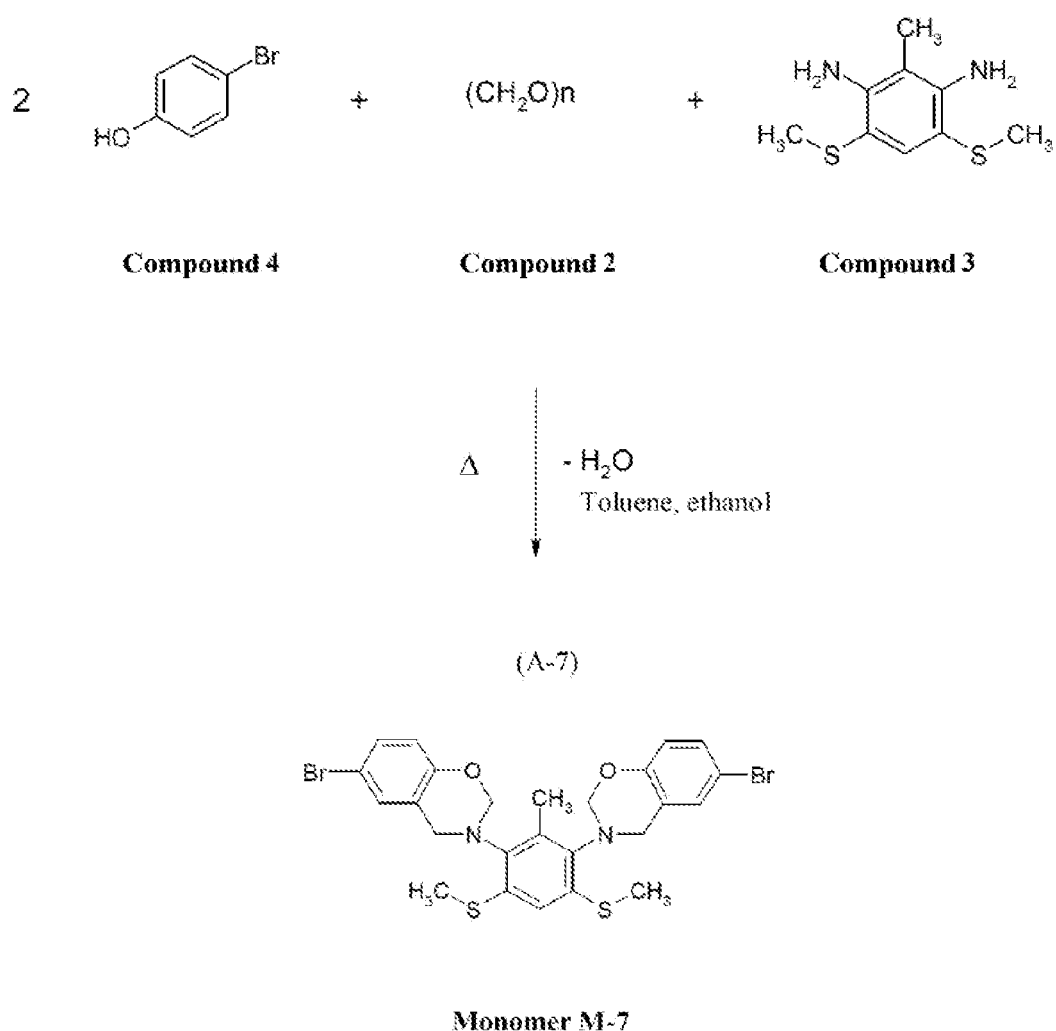
Figure 11:
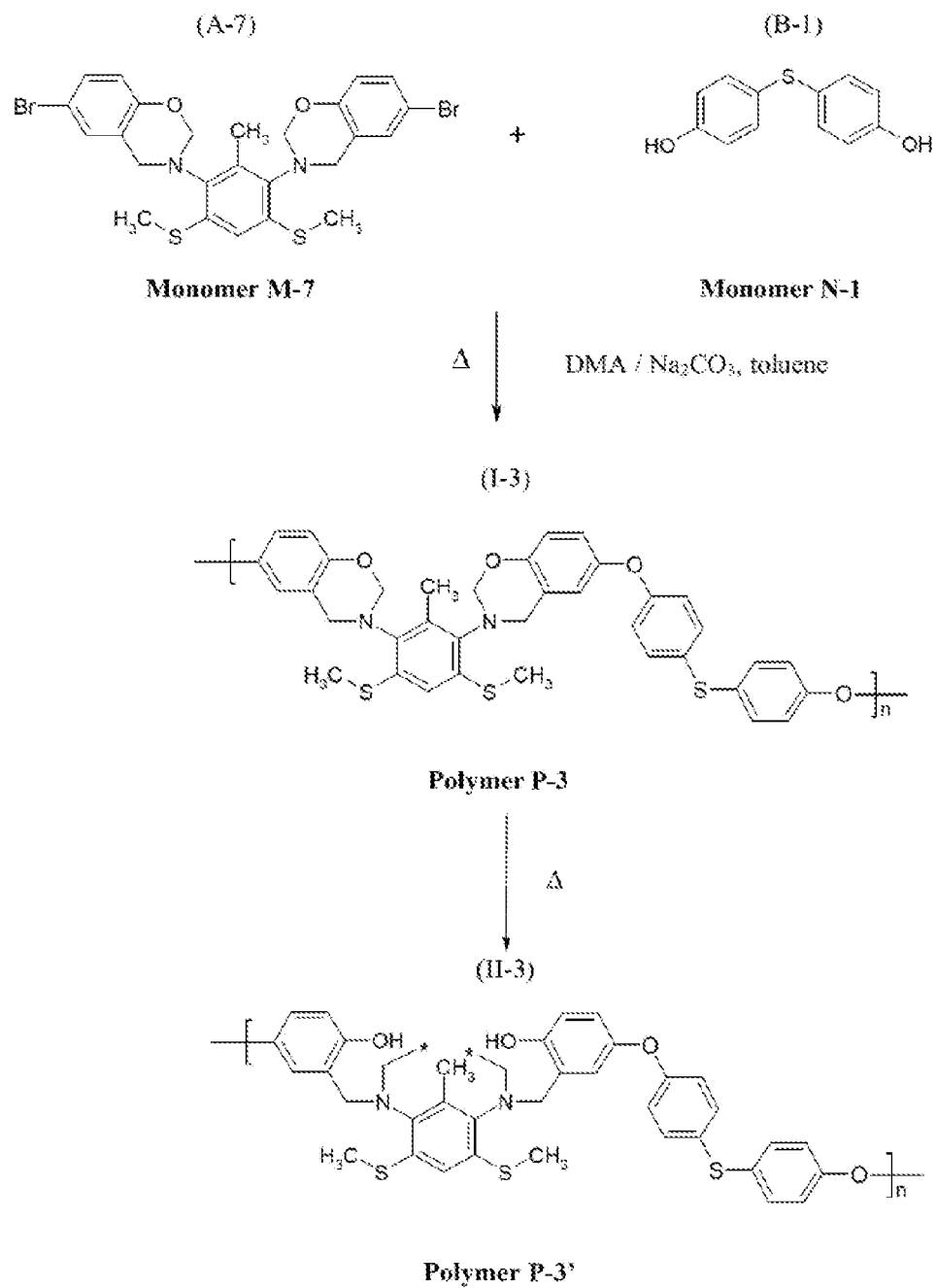

The invention and the advantages thereof will be easily understood in the light of the detailed description and the implementation examples which follow, and also of FIGS. 1 to 11, which represent or depict:

the general principle for the synthesis of a benzoxazine compound starting from three compounds, phenol, formaldehyde and amine (R=residue of the amine) (FIG. 1a); the (ring-opening) mechanism for opening, by heat input, the oxazine ring of such a benzoxazine compound (FIG. 1b);

a general scheme for the synthesis, starting from a specific phenol (the symbol "G" will be described in detail later), paraformaldehyde and a specific aromatic diamine sulfide, of a benzoxazine in accordance with the invention of formula (A-0) (Monomer denoted by "M-0") that can be used for the synthesis of a polybenzoxazine sulfide (FIG. 2);

a possible scheme for the synthesis, starting from a halogenated phenol (the symbol "Hal" representing a halogen), p-formaldehyde and the preceding specific aromatic diamine sulfide, of a particular halogenated benzoxazine in accordance with the invention of formula (A-1) (Monomer denoted by M-1) that can be used for the synthesis of a polybenzoxazine (FIG. 3);

another possible scheme for the synthesis, starting from another specific phenol (the symbol "A" will be described in detail later), p-formaldehyde and the preceding specific aromatic diamine sulfide, of another benzoxazine of formula (A-2) (Monomer denoted by M-2) in accordance with the invention (FIG. 4);

another possible scheme for the synthesis, starting from a halogenated phenol, p-formaldehyde and a particular example of an aromatic diamine sulfide, of another example of a particular halogenated benzoxazine in accordance with the invention of formula (A-3) (Monomer denoted by M-3) (FIG. 5);

another possible scheme for the synthesis, starting from another specific phenol, p-formaldehyde and the preceding specific example of an aromatic diamine sulfide, of another example of a benzoxazine in accordance with the invention of formula (A-4) (Monomer denoted by M-4) (FIG. 6);

another possible scheme for the synthesis, starting from a particular example of a phenol (Compound 1: methoxyphenol bearing ethylenic unsaturation), p-formaldehyde (Compound 2) and the preceding particular example (Compound 3) of an aromatic diamine disulfide, of another example of a benzoxazine in accordance with the invention of formula (A-5) (Monomer denoted by M-5) (FIG. 7);

a scheme for the general synthesis of an example of a polybenzoxazine sulfide (Polymer denoted by P-1), starting from the preceding halogenated benzoxazine in accordance with the invention of formula (A-6) (Monomer M-6) and from another monomer of general formula (B) (Monomer denoted by N) of the aromatic diol or thiol type; and also this example of a polybenzoxazine sulfide (Polymer denoted here by P-1') once its oxazine rings have been opened after heat treatment of the polymer P-1 (FIG. 8);

a scheme for the synthesis of another polybenzoxazine (Polymer P-2'), with its oxazine rings opened, obtained by homopolymerization of the particular halogenated benzoxazine of formula (A-5) (Monomer M-5) (FIG. 9);

an example of synthesis, starting from brominated phenol (compound 4), p-formaldehyde (compound 2) and a specific aromatic diamine disulfide (compound 3), of a particular brominated benzoxazine of formula (A-7) (Monomer denoted by M-7) which may be used for the synthesis of polybenzoxazines (Polymer P-3 and P-3' of FIG. 11) (FIG. 10);

finally, an example of synthesis of a polybenzoxazine sulfide (Polymer by P-3), starting from the preceding particular halogenated benzoxazine according to the invention of formula (A-7) (Monomer M-7) and from another particular monomer of formula (B-1) (Monomer N-1) of the sulfur-based aromatic diol type (bearing a thioether function), and also the structure of this polymer once its oxazine rings have been opened (Polymer denoted by P-3') (FIG. 11).

5. DETAILED DESCRIPTION OF THE INVENTION

It will first of all be recalled that benzoxazines are compounds of general formula:

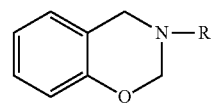

The appended FIG. 1a recalls the general principle of the synthesis of a benzoxazine, in this instance starting (condensation reaction) from one molecule of phenol, from two molecules of formaldehyde and from an amine (R denoting the residue of the amine), with elimination of two molecules of water.

FIG. 1b for its part recalls the mechanism for opening the oxazine ring (ring-opening) of such a compound during a heat input (represented by the symbol A).

Numerous benzoxazine compounds or monomers can thus be synthesized using various phenols and amines according to their types of substituents. These substituting groups may subsequently provide polymerizable sites and make possible the synthesis of various benzoxazine polymers (or polybenzoxazines).

Benzoxazines and polybenzoxazines which result therefrom are products which are today well known to a person skilled in the art; to cite but a few publication examples, mention may be made of the papers "*Polybenzoxazines—New high performance thermosetting resins: synthesis and properties*"; N. N. Ghosh et al., Prog. Polym. Sci., 32 (2007), 1344-1391, or "*Recent Advancement on Polybenzoxazine—A Newly Developed High Performance Thermoset*", Y. Yaggi et al., J. Polym. Sci. Part A: Polym. Chem.: Vol. 47 (2009), 5565-5576, and also, for example, of the patents or patent applications U.S. Pat. No. 5,543,516 and WO 2013/148408.

As explained in detail in the above documents, polybenzoxazines have the remarkable ability, at high temperature (for example, typically greater than 150° C., or even greater than 200° C., depending on their particular microstructure), to open their oxazine rings and to thus result in thermosetting polyphenol resin structures.

The specific benzoxazine that is the subject of the invention (referred to as Monomer M in the present application) is of the benzoxazine sulfide type; it corresponds to the following generic formula (A):

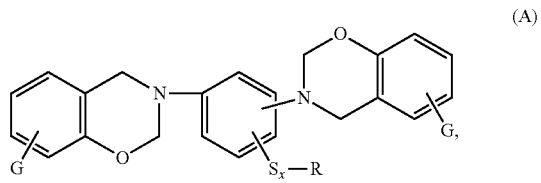

(A)

in which each benzene nucleus of the two oxazine rings bears at least one (i.e. one or more) radical G; the benzoxazine itself thus bears at least two radicals G.

The (at least) two radicals G, which may be identical or different, are chosen from the group consisting of:
  halogens;
  groups —$OR_1$, —$SR_1$, —$NR_2R_3$; $R_1$, $R_2$ and $R_3$, which may be identical or different, representing an alkyl containing 1 to 4 carbon atoms; and
  aliphatic hydrocarbon-based groups including 1 to 8 carbon atoms, or cycloaliphatic hydrocarbon-based groups including 3 to 8 carbon atoms, or aromatic hydrocarbon-based groups including 6 to 12 carbon atoms; these saturated or ethylenically unsaturated hydrocarbon-based groups also optionally including at least one heteroatom chosen from O, S, N and P.

In this formula (A), the two oxazine rings are connected together via a central aromatic group, the benzene ring or nucleus of which (also referred to as the central benzene ring or nucleus) bears one, two, three or four groups of formula —$S_x$—R in which "x" is an integer from 1 to 8 and R represents hydrogen or a hydrocarbon-based group including 1 to 10 carbon atoms and optionally a heteroatom chosen from O (oxygen), S (sulfur), N (nitrogen) and P (phosphorus).

Similarly, it may be noted in this formula (A) that the two nitrogen atoms of the oxazine rings are, relative to each other, in any position (i.e. ortho, meta or para) on the central benzene nucleus. However, preferably, these two nitrogen atoms are in the meta-position relative to each other; in other words, the benzoxazine (Monomer in this case denoted by M-0) of the invention then preferentially corresponds to the generic formula (A-0) below:

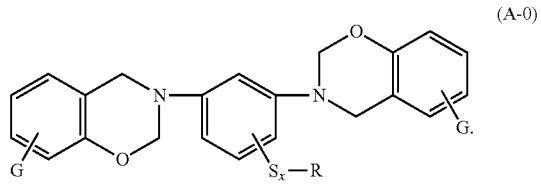

(A-0)

The appended FIG. 2 gives the scheme for the general synthesis of this benzoxazine of formula (A-0), with heat input and with elimination of water, starting from a specific phenol bearing at least one (i.e. one or more) radical G, paraformaldehyde and, finally, a specific aromatic diamine sulfide of formula:

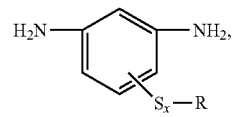

in which formula, needless to say, the benzene ring bears one, two, three or four groups of formula —$S_x$—R as defined previously, and may bear other optional substituents (by way of example a methyl or ethyl group).

Preferentially, in this benzoxazine of formula (A) or (A-0), the central benzene nucleus bears two groups of formula —$S_x$—R, these two groups more preferentially being in the meta-position relative to each other on this central benzene nucleus. According to another preferential embodiment, "x" is within a range from 1 to 4, more preferentially equal to 1 or 2. R is preferentially an alkyl more preferentially containing 1 to 5 carbon atoms, even more preferentially a methyl or ethyl, in particular a methyl.

The polybenzoxazine (Polymer P), derived from the benzoxazine of the invention of formula (A) described previously, thus has for its part the essential feature of including structural repeating units including at least one unit corresponding to formula (I) (before opening of the oxazine rings) or formula (II) (after ring opening) below:

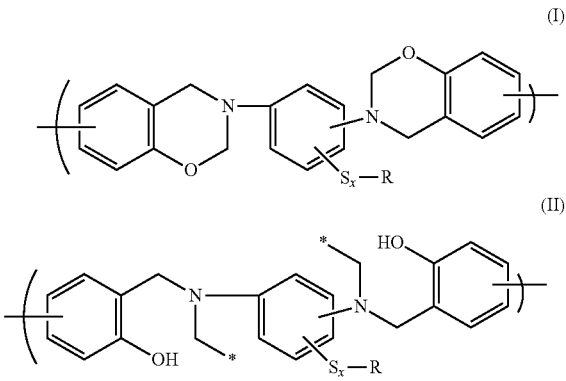

The term "polymer" should be understood in the present patent application as meaning any homopolymer or copolymer, notably block copolymer, with repeating structural units including at least one unit of formula (I) or (II) above; needless to say, the polymer may include both units of formula (I) and units of formula (II).

In formula (II) above, a person skilled in the art will immediately understand that the two symbols "*" (which may be identical or different) represent any attachment of the unit to a carbon atom or to a heteroatom (preferably chosen from O, S, N and P), this attachment or bond resulting from the opening of the oxazine rings during a sufficient input of heat (A).

In addition, in the above formulae (I) and (II), as for the monomer of formula (A), one or more hydrogen atoms of at least one or of each benzene nucleus of the two oxazine rings, and also those of the central benzene ring, may optionally also be substituted with various substituents (by way of example a methyl or ethyl group), notably with functional groups (by way of example a vinyl group) capable of promoting the adhesion of the polymer to the metal and/or to the rubber.

Similarly, as for the preceding monomer of formula (A), it may be noted in these formulae (I) and (II) that the two nitrogen atoms of the oxazine rings are, relative to each other, in any position (i.e. ortho, meta or para) on the central benzene nucleus which separates them.

However, preferably, these two nitrogen atoms are in the meta-position relative to each other on the central benzene nucleus; in other words, the polybenzoxazine that is derived from the benzoxazine compound of the invention then includes at least repeating structural units including (at least) one unit corresponding to formula (I-bis) (before opening of the oxazine rings) or formula (II-bis) (after opening of the rings) below:

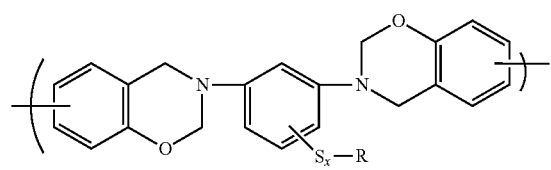

(I-bis)

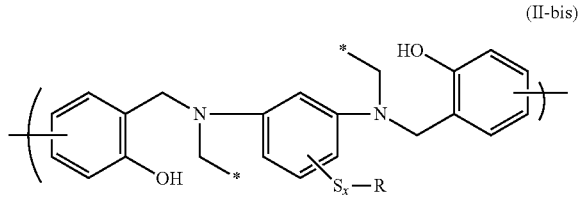

(II-bis)

In the preceding formula (A) or (A-0) of the compound of the invention, preferably, each benzene nucleus of the two oxazine rings bears only one radical G or at most two, more preferentially only one radical G.

This radical (a single radical G) is even more preferentially located in the para position relative to the oxygen of the oxazine ring; the benzoxazine of the invention in this case thus corresponds to the following formula (denoted (A-6) in the attached FIG. 8):

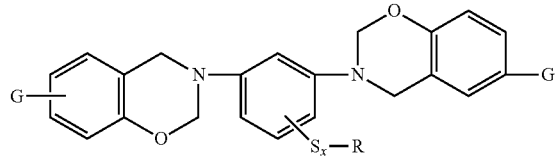

In such a case, it will be understood that the polybenzoxazine that is derived from the compound of the invention thus has for its part the essential feature of including at least repeating structural units including (at least) one unit corresponding to formula (I-a) (before opening of the oxazine rings) or formula (II-a) (after ring opening) below:

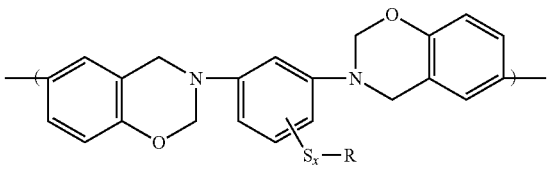

(I-a)

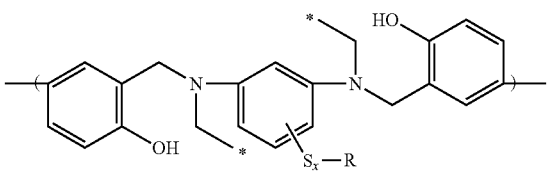

(II-a)

Even more preferentially, "x" is equal to 1 and R represents a methyl.

Thus, as examples of aromatic diamine sulfides that are suitable for the synthesis of a benzoxazine of formula (A) or (A-0) according to the invention in which, according to a particularly preferential embodiment, "x" is equal to 1 and R represents a methyl, mention will be made in particular of the compounds 3,5-bis(methylthio)-2,4-toluenediamine, 3,5-bis(methylthio)-2,6-toluenediamine and mixtures thereof, corresponding, respectively, to formulae (a) and (b) below:

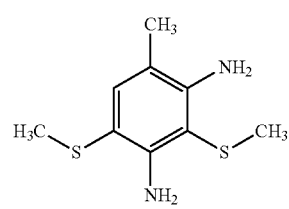

(a)

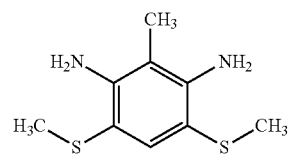

(b)

In other words, according to a particularly preferential embodiment, if the benzoxazine of formula (A-0) is derived from at least one of the above two isomers or from mixtures thereof, then the polybenzoxazine that is derived from the compound of the invention includes repeating units including at least one unit corresponding to formula (I-a-1) or (I-b-1) (before opening of the oxazine rings), (II-a-1) or (II-b-1) (after ring opening) below:

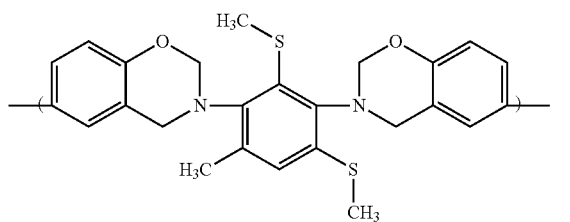

(I-a-1)

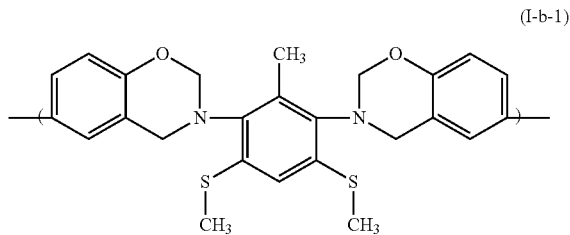

(I-b-1)

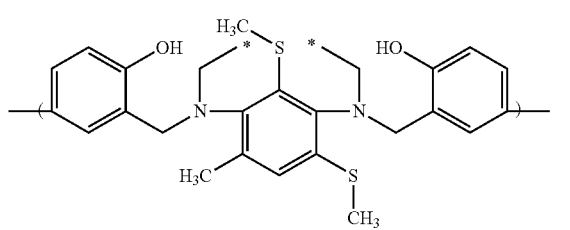

(II-a-1)

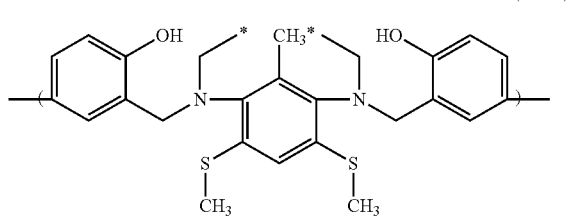

(II-b-1)

According to a preferential embodiment of the invention, the (at least two) radicals G, which may be identical or different, represent a halogen such as bromine, chlorine, fluorine or iodine.

The appended FIG. 3 is a scheme of the general synthesis, with heat supply and with elimination of water, starting from a halogenated phenol bearing at least one (i.e. one or more) halogen (represented by the symbol "Hal"), p-formaldehyde and the specific aromatic diamine sulfide of the preceding FIG. 2, of a particular halogenated benzoxazine of formula (A-1) (Monomer denoted by M-1), in accordance with the invention, which may be used for the synthesis of a polybenzoxazine. This halogen (Hal) is more preferentially bromine or chlorine, even more preferentially bromine; the latter even more preferentially being in the para position relative to the oxygen of each oxazine ring.

According to another preferential embodiment, the (at least two) radicals G, which may be identical or different, represent a group chosen from —$OR_1$, —$SR_1$, —$NR_2R_3$; $R_1$, $R_2$ and $R_3$, which may be identical or different, representing an alkyl containing 1 to 4 carbon atoms.

According to another preferential embodiment, the (at least two) radicals G, which may be identical or different, represent an aliphatic hydrocarbon-based group (represented by the symbol "A") including 1 to 8 carbon atoms, or a cycloaliphatic hydrocarbon-based group including 3 to 8 carbon atoms, or an aromatic hydrocarbon-based group including 6 to 12 carbon atoms, this saturated or ethylenically unsaturated hydrocarbon-based group "A" being able optionally to include a (at least one) heteroatom chosen from O, S, N and P.

The appended FIG. 4 is a scheme of the general synthesis, with heat supply and with elimination of water, starting from a halogenated phenol bearing at least one (i.e. one or more) such group "A", paraformaldehyde and the specific aromatic diamine sulfide of the preceding FIGS. 2 and 3, of a particular benzoxazine according to the invention of formula (A-2) (Monomer denoted by M-2) which may be used for the synthesis of a polybenzoxazine.

FIG. 5 is another possible scheme for the synthesis, starting from a halogenated phenol, paraformaldehyde and a specific example of an aromatic diamine disulfide, namely 3,5-bis(methylthio)-2,6-toluenediamine of the preceding formula (b), of another example of a particular halogenated benzoxazine in accordance with the invention of formula (A-3) (Monomer denoted by M-3) that can be used for the synthesis of a polybenzoxazine.

FIG. 6 is another possible scheme for the synthesis, starting from another phenol (the symbol "A" has been described previously), paraformaldehyde and 3,5-bis(methylthio)-2,6-toluenediamine of the preceding formula (b), of another example of a benzoxazine of formula (A-4) (Monomer denoted by M-4) that can be used for the synthesis of a polybenzoxazine.

According to a preferential embodiment, the (at least two) groups "A", which may be identical or different, represent an saturated or ethylenically unsaturated aliphatic hydrocarbon-based group, including 1 to 6 and in particular 1 to 4 carbon atoms, which may optionally include at least one (i.e. one or more) heteroatom chosen from O, S, N and P.

Thus, according to another particular and preferential embodiment, the benzoxazine disulfide of the invention corresponds at least partly to one of the two formulae (A-5) and (A-5bis) (Monomers denoted, respectively, by M-5 and M-5bis) below:

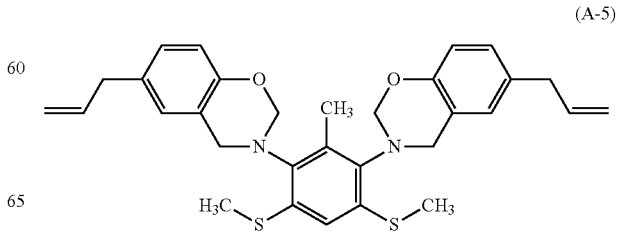

(A-5)

-continued (A-5bis)

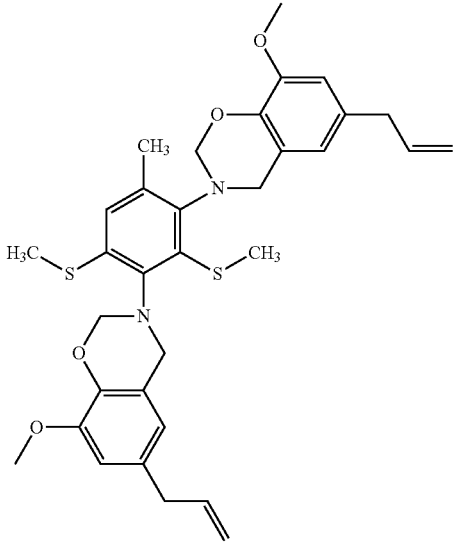

FIG. 7 is a particular case of FIG. 6 which describes another scheme for the synthesis, starting this time from a particular example of a phenol (Compound 1) corresponding to such a preferential definition (in this case, phenol bearing an ethylenic unsaturation and a methoxyl group), paraformaldehyde (Compound 2) and the particular example of the preceding aromatic diamine disulfide (Compound 3), of another example of a benzoxazine in accordance with the invention of formula (A-5) (Monomer denoted by M-5) which may be used in particular for the synthesis of a polybenzoxazine sulfide.

A person skilled in the art is well aware of how to widely adapt specific formula (A) or (A-0) of the benzoxazine of the invention serving as starting monomer for the synthesis of polybenzoxazines, by notably varying the formulae of the phenol (bearing the radical(s) G) and of the diamine sulfide (bearing the group(s) of formula —$S_xR$).

As examples of preferential aromatic diamine sulfides, mention has already notably been made of the compounds 3,5-bis(methylthio)-2,4-toluenediamine, 3,5-bis(methylthio)-2,6-toluenediamine, and mixtures thereof.

As examples of phenol compounds (in this case, for example, methoxyphenols) bearing groups "A" of the saturated or ethylenically unsaturated aliphatic hydrocarbon-based type, including 1 to 6 and in particular 1 to 4 carbon atoms, which may optionally include at least one (i.e. one or more) heteroatom chosen from O, S, N and P, examples that may be mentioned include the following compounds:

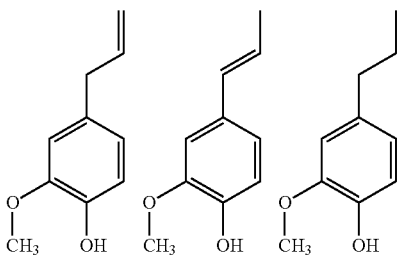

-continued

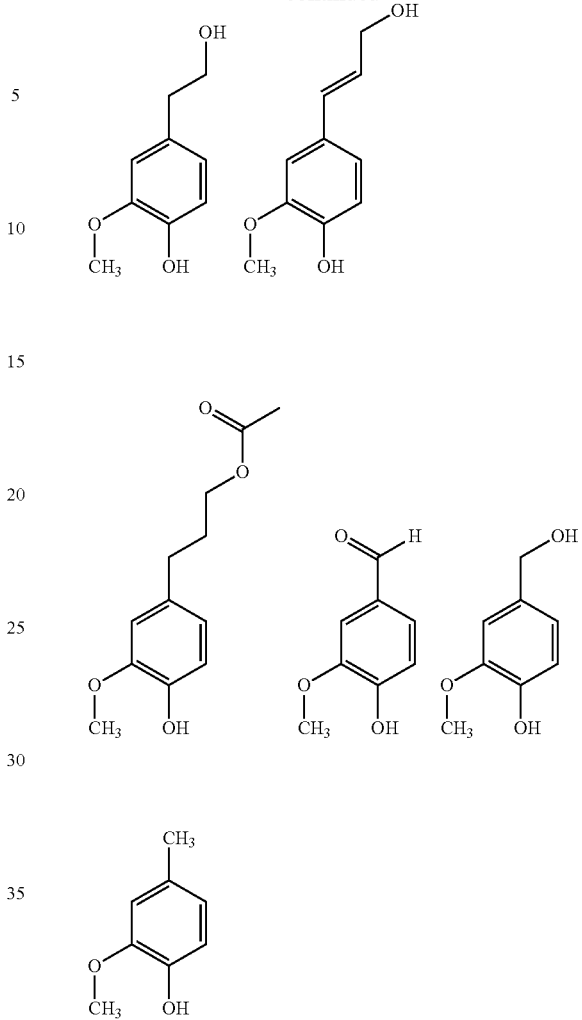

The benzoxazine in accordance with the invention of formula (A) described previously is particularly intended (as Monomer M) for the synthesis of a polybenzoxazine by polycondensation, in particular by polycondensation with at least one aromatic diol or thiol compound as second monomer ("Monomer N").

This aromatic diol or thiol compound more preferentially corresponds to formula (B):

$$HX_1—Ar_1—Z—Ar_2—X_2H \quad (B)$$

in which:

$X_1$ and $X_2$, which may be identical or different, represent O or S;

$Ar_1$ and $Ar_2$, which may be identical or different, represent an aromatic group, preferably phenylene;

Z represents O or $(S)_n$, the symbol "n" representing an integer greater than or equal to 1.

Thus, according to one particularly preferred embodiment, the polybenzoxazine that is derived from the benzoxazine sulfide of the invention is characterized by repeat units including at least one unit corresponding to the particular formulae (I-1) (before opening of the oxazine rings) or (II-1) (after ring opening):

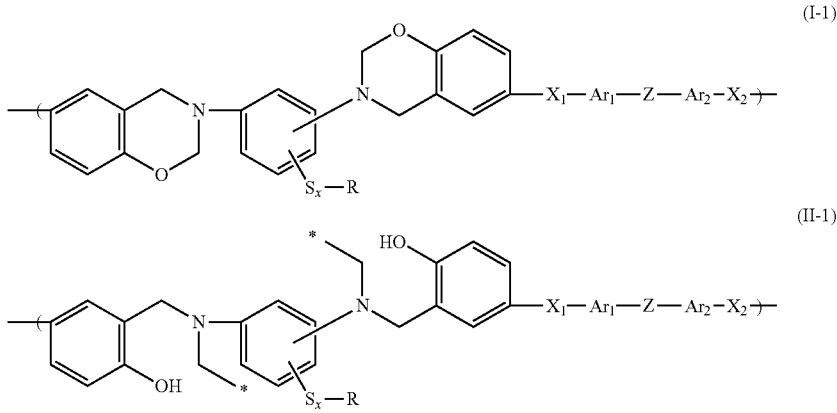

(I-1)

(II-1)

In this case also, it is clearly noted that, in the above formulae, the two nitrogen atoms of the oxazine rings are, relative to each other, in any position (i.e. ortho, meta or para) on the central benzene nucleus which separates them.

However, even more preferentially, in the above formulae (I-1) and (II-1) above, these two nitrogen atoms are in the meta-position relative to each other on the central benzene nucleus which separates them. In other words, the polybenzoxazine that is derived from the benzoxazine of the invention then includes repeating structural units including (at least) one unit corresponding to formula (I-1bis) (before opening of the oxazine rings) or formula (II-1bis) (after ring opening) below:

In the general formulae (I-1), (II-1), (I-1bis) or (II-1bis) above, preferentially at least one of the following features is satisfied:

$Ar_1$ and $Ar_2$ each represent an unsubstituted phenylene group;

$X_1$ and $X_2$ each represent either a sulfur atom, or an oxygen atom;

Z represents O or S (i.e. "n" equal to 1), more preferentially S.

More preferentially, it is all of the preferential features above which are simultaneously satisfied.

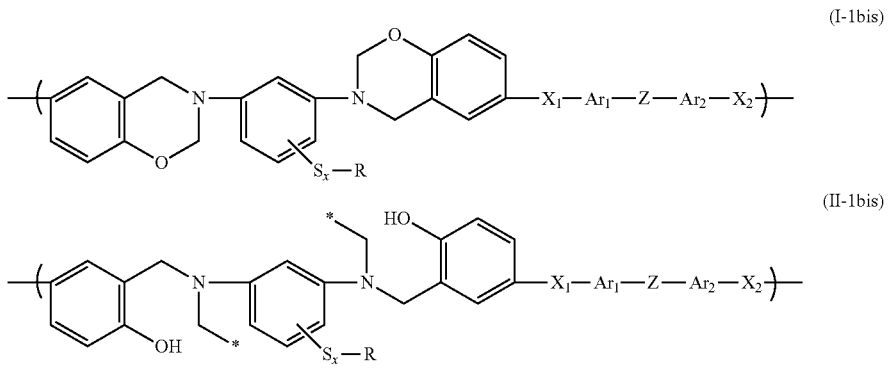

(I-1bis)

(II-1bis)

In the above formulae (I-1), (II-1), (I-1bis) and (II-1bis), one or more hydrogen atoms of at least one or of each aromatic nucleus $Ar_1$ and $Ar_2$ could be substituted with various substituents, which may be identical or different, for example functional groups capable of promoting the adhesion of the polymer to the metal and/or to the rubber.

FIG. 8 is a scheme for the general synthesis of a polybenzoxazine sulfide (Polymer denoted by P-1) of formula (I-1bis) above, in accordance with the process of the invention, by polycondensation of the preceding halogenated benzoxazine according to the invention of formula (A-6) (Monomer M-6) with another monomer of general formula (B) (Monomer denoted by "N") of the aromatic diol or thiol type; and also this example of a polybenzoxazine sulfide (Polymer denoted here by P-1' of formula II-1bis) once its oxazine rings have been opened after heat treatment of the polymer P-1.

As preferential examples, the compound of the preceding formula (B) corresponds to at least one of the particular formulae (B-1), (B-2) or (B-3) below:

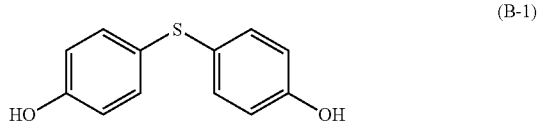

(B-1)

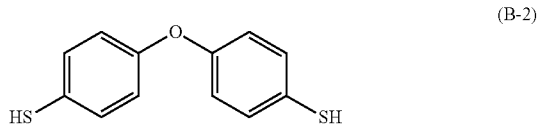

(B-2)

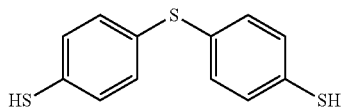
(B-3)

According to another particular and preferential embodiment, the polybenzoxazine polymer may be obtained by homopolymerization of a benzoxazine of formula (A) or (A-0) as described above.

Thus, FIG. 9 illustrates a scheme for the synthesis of another polybenzoxazine (Polymer P-2' of formula II-2), with its oxazine rings opened, this time obtained by simple homopolymerization of the particular halogenated benzoxazine according to the invention of the preceding formula (A-5) (Monomer M-5).

According to another particular and preferential embodiment, the benzoxazine of the invention is a brominated benzoxazine disulfide which corresponds at least partly to one of the two formulae (A-7) and (A-7bis) (Monomers denoted, respectively, by M-7 and M-7bis) below:

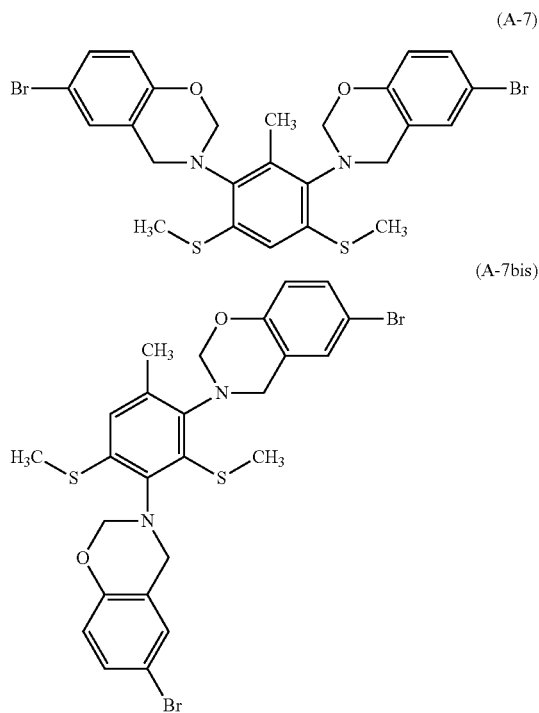

(A-7)

(A-7bis)

FIG. 10 precisely gives an example of synthesis, starting from the brominated phenol (compound 4), p-formaldehyde (compound 2) and 3,5-bis(methylthio)-2,6-toluenediamine (compound 3), of this brominated benzoxazine disulfide of formula (A-7) (Monomer denoted by M-7) which may be used for the synthesis of polybenzoxazines (Polymer P-3 and P-3' of FIG. 11) in accordance with the process of the invention.

In these examples of FIG. 10, as for the preceding FIGS. 7 to 9, it is noted in particular, according to a particularly preferential embodiment of the invention already indicated, that each benzene nucleus of the two oxazine rings of the benzoxazine of formula (A) bears only one halogen (Hal), more preferentially bromine, located in the para position relative to the oxygen of the oxazine ring.

Finally, FIG. 11 describes the synthesis of a polybenzoxazine sulfide (Polymer P-3) starting from the particular halogenated benzoxazine of formula (A-7) (Monomer M-7) above and from another particular monomer of formula (B-1) (Monomer N-1) of the sulfur-based aromatic diol type (bearing a thioether function), and also the structure of this polymer once its oxazine rings have been opened (Polymer denoted by P-3').

The syntheses of FIGS. 7, 10 and 11 will be described in greater detail in the implementation examples that follow.

Typically, the polybenzoxazine derived from the benzoxazine compound of the invention may include from ten to several hundred, preferably from 50 to 300, structural units bearing units of formula (I) and/or (II), in particular structural units as represented as examples in FIGS. 8, 9 and 11.

This polybenzoxazine derived from the benzoxazine of the invention is advantageously usable, as adhesion primer or as sole adhesive layer, for coating a metal substrate, at the very least a substrate of which at least the surface is at least partly metallic, and for making the latter adhere to rubber. It is most particularly usable on any type of metallic reinforcement, for instance a wire, film or cable made of steel, notably of carbon steel, intended in particular for reinforcing an unsaturated rubber matrix such as natural rubber. In order to adhere the rubber to the polybenzoxazine layer, use may be made of any known adhesive system, for example a conventional textile adhesive of "RFL" (resorcinol-formaldehyde-latex). A person skilled in the art will readily understand that the connection between the metal substrate provided with its polybenzoxazine layer and the rubber layer with which it is in contact will be definitively provided during the final curing (crosslinking) of the rubber article in question.

6. EXAMPLES OF THE INVENTION

In the present patent application, unless expressly indicated otherwise, all the percentages (%) shown are mass percentages.

The following tests firstly describe the synthesis of two examples of benzoxazine compounds (Monomers M-5 and M-7) in accordance with the invention, then that of a polybenzoxazine (Polymer P-3) starting from the Monomer M-7. Lastly, adhesion tests are performed to illustrate the excellent adhesive performance of the polybenzoxazines derived from the compounds of the invention.

5.1. Synthesis of a Benzoxazine Sulfide According to the Invention (Monomer M-5)

For this synthesis, a 100-ml three-necked round-bottomed flask, equipped with a thermometer, a nitrogen inlet, a magnetic stirrer and a condenser, is provided.

The synthesis is performed according to the procedure depicted in FIG. 7, as explained in detail below, starting with three compounds: a specific ethylenically unsaturated phenol bearing a methoxyl group (compound 1; eugenol; Aldrich product E51791), paraformaldehyde (compound 2; Aldrich product 158127) and an aromatic diamine disulfide (compound 3; 3,5-bis(methylthio)-2,6-toluenediamine), in the presence of two solvents (anhydrous toluene and anhydrous ethanol).

Compound 3 was isolated, by chromatography on silica gel, from the product Ethacure 300 (supplier: Albemarle, Belgium), available in the form of a relatively viscous liquid of brownish colour; it is composed to approximately 96% of a mixture of 3,5-bis(methylthio)-2,4-toluenediamine and 3,5-bis(methylthio)-2,6-toluenediamine isomers (weight ratio of approximately 4/1 according to chromatographic analysis).

Compound 1 (2 eq., 4.93 g, i.e. 30 mmol) and then ethanol (51 ml) are poured into the round-bottomed flask. The presence of ethanol is important in this instance, preventing the formation of an unstable triazine-type intermediate product. Compound 3 (1 eq., 3.215 g, i.e. 15 mmol), compound 2 (4 eq., 1.80 g, i.e. 60 mmol) and finally the toluene (102 ml) are subsequently introduced with stirring. The reaction medium is heated (approximately 75° C.) at reflux for 4 h and, after distilling off the ethanol at about 100° C. over 16 hours, the solvents and volatile residues are then finally distilled off at 40° C. (under a vacuum of 20 mbar) for evaporation. The final product is then washed (100 ml of methanol) and dried.

This powder is placed in methanol (50 ml per 4 g of powder) and the mixture is heated at reflux (65° C.) for 30 min. The solution is then left to cool to room temperature (approximately 20° C.) for crystallization of the monomer. The solid product obtained is isolated by filtration (Büchner filter). After drying in a vacuum oven at 50° C. overnight, a powder is thus obtained, the $^1$H NMR spectrum (500 MHz) (solvent: d8-THF) of which confirmed the chemical structure of the Monomer M-5 thus synthesized, with the following results:

2.07 (s, 3H), 2.38 (s, 6H), 3.25 (t, 4H), 3.71 (s, 6H), 3.94-4.01 (t, 2H), 4.58-4.64 (dd, 2H), 4.81-4.86 (dd, 2H), 4.96-5.05 (m, 6H), 5.85-5.97 (m, 2H), 6.37-6.40 (d, 2H), 6.55 (s, 2H), 6.72 (s, 1H).

5.2. Synthesis of Another Benzoxazine Sulfide According to the Invention (Monomer M-7)

As previously, for this synthesis, a 100-ml three-necked round-bottomed flask, equipped with a thermometer, a nitrogen inlet, a magnetic stirrer and a condenser, is provided.

The synthesis is performed according to the procedure depicted in FIG. 10, as explained in detail below, starting with three compounds: a halogenated phenol (compound 4; 4-bromophenol; Aldrich product B75808), p-formaldehyde (compound 2; Aldrich product 158127) and an aromatic diamine disulfide (compound 3; 3,5-bis(methylthio)-2,6-toluenediamine), isolated as before from the product Ethacure 300 in the presence of two solvents (anhydrous toluene and anhydrous ethanol).

Compound 4 (2 eq., 2.6 g, i.e. 15 mmol) and then ethanol (23 ml) are poured into the round-bottomed flask. The presence of ethanol is important in this instance, preventing the formation of an unstable triazine-type intermediate product. Compound 3 (1 eq., 1.6 g, i.e. 7.5 mmol), compound 2 (4 eq., 0.90 g, i.e. 30 mmol) and finally the toluene (46 ml) are subsequently introduced with stirring. The reaction medium is heated (approximately 75° C.) at reflux for 16 h and then the solvents and volatile residues are distilled off at 110° C. under vacuum (1 mbar) for evaporation.

The final product is then placed in methanol (50 ml per 4.5 g of product) and the mixture is heated at reflux (65° C.) for 30 min. The solution is then left to cool to room temperature (approximately 20° C.) for crystallization of the monomer. The solid product obtained is isolated by filtration (Büchner filter). A yellow powder is thus obtained, after drying in a vacuum oven at 50° C. overnight (reaction yield equal to approximately 82%).

The $^1$H NMR spectra (500 MHz) of the Monomer M-7 thus synthesized, dissolved in a deuterated solvent, confirmed its chemical structure, with the following results:

in d8-THF: 2.06 (s, 3H), 2.39 (s, 6H), 4.03-4.14 (t, 2H), 4.59-4.63 (d, 2H), 4.87-4.91 (dd, 2H), 5.01-5.05 (dd, 2H), 6.71-6.74 (d, 2H), 6.81 (s, 1H), 7.15-7.21 (m, 4H);

in $CD_2Cl_2$:
2.06 (s, 3H), 2.39(s, 6H), 4.03-4.14 (t, 2H), 4.53-4.58 (dd, 2H), 4.92-4.95 (dd, 2H), 5.00-5.04 (dd, 2H), 6.68 (s, 1H), 6.74-6.77(d, 2H), 7.14-7.15 (d, 2H), 7.21-7.24 (dd, 2H).

5.3. Synthesis of a Polybenzoxazine Polysulfide (Polymer P-3)

This synthesis is performed according to the procedure depicted in the FIG. 11, as described in detail below, starting with two monomers: the benzoxazine obtained in the preceding step (Monomer M-7) and the sulfur-bearing aromatic diol of formula (B-1) (4,4'-thiodiphenol; Monomer N-1); this being in the presence of sodium carbonate ($Na_2CO_3$; Sigma Aldrich product 13418), and the (anhydrous) solvents DMA (N,N-dimethylacetamide; Sigma Aldrich product 38839) and toluene (Acros Organics product No. 364411000). The two monomers (M-7 and N-1) are dried beforehand under vacuum (10 mbar) at 60° C. overnight, and likewise for the sodium carbonate but at a temperature of 150° C.

The synthesis is performed in a 100-ml four-necked round-bottomed flask, equipped with a nitrogen inlet, a thermometer, a magnetic stirrer and a Dean-Stark separator surmounted by a condenser and by a distillation bridge (provided with a heating mantle). The apparatus is dried under vacuum using a hot air gun until the thermometer reaches a temperature of at least 100° C. in the reaction flask. The system is left to cool to room temperature (20° C.) and the apparatus is then placed under a stream of nitrogen throughout the synthesis.

First of all, the Monomer M-7 (1 eq., 1.5 g, i.e. 2.79 mmol) of formula (A-7) and then the Monomer N-1 of formula (B-1) (1 eq., 0.61 g, i.e. 2.79 mmol) are then introduced into the round-bottomed flask. This is followed by addition of 20 ml of DMA (solvent of both monomers) and then, as base, of $Na_2CO_3$ (3 eq., 0.89 g, i.e. 8.36 mol) suspended in 4 ml of toluene. The system is purged under $N_2$ for 5 min and the reaction medium is then heated to 105° C. Once this temperature is reached (heating mantle temperature of approximately 115° C.), the distillation bridge of the Dean-Stark apparatus is heated to 110° C. (with the heating mantle) in order to facilitate the azeotropic distillation (water/toluene distillation) performed for approximately 90 min. The temperature of the reaction medium is then gradually increased, in stages of 10° C. every 30 min, until 130° C. is reached. The reaction medium is left at this temperature for 17 h and is then left to cool to room temperature (20° C.). The reaction mixture is subsequently distilled at 90° C. (vacuum 3 mbar) to remove the solvents and volatile residues, and the solid precipitate thus obtained is then washed with 250 ml of distilled water; during this washing, to extract the carbonate, acid (1% aqueous HCl) is added dropwise until neutral pH is reached. The precipitate is once again washed with 100 ml of distilled water and dried under vacuum at 80° C. overnight (approximately 12 h); the Polymer P-3 of FIG. 11 was thus obtained, as attested to by the $^1$H NMR analysis (500 MHz).

The Polymer P-3 of FIG. 11 was thus obtained, as attested to by the $^1$H NMR analysis (500 MHz) in the solvent d8-THF, which gave the following results:

1.92 (s, 3H), 2.26 (s, 6H), 3.74-3.81 (m, 4H), 4.01-4.03 (t, 2H), 4.75-5.01 (m, 2H), 6-15-6.75 (m, 4H), 6.90-7.45 (br, 11H).

This Polymer P-3, in the form of a pale yellow powder, was also analysed by DSC (Differential Scanning Calorimetry) between −80° C. and +350° C. with a ramp of 10° C./min (Mettler Toledo DSC "822-2" machine; nitrogen atmosphere). The analysis showed, in the first pass (between −80° C. and +350° C.), an apparent glass transition (Tg) at 163° C. followed by exothermicity (corresponding to the opening of the oxazine rings and to the crosslinking of the polymer) above 200° C., with two maxima at approximately 270° C. and 299° C. During the second and third DSC passes, performed between −80° C. and +350° C., no apparent glass transition was visible.

5.4. Test of Adhesion in a Metal/Rubber Composite

A portion (325 mg) of the Polymer P-3 prepared above was dissolved in 8 ml of DMPU (1,3-dimethyl-3,4,5,6-tetrahydro-2(1H)-pyrimidinone; Sigma Aldrich product 41661) with 10% by weight of "DY 9577 ES" accelerator (Huntsman product), this being in order to form a solution, a fraction (0.6 ml) of which was subsequently deposited uniformly on a brass tape (film) having dimensions of 10 cm×2.5 cm and a thickness of 0.5 mm; the assembly was placed in an oven at 175° C. (air ventilation) for 5 min and then for an additional 5 min at 230° C. under vacuum in order, firstly, to remove any trace of solvent and, secondly, to at least partially (that is to say, completely or partially) open the oxazine rings of the polymer, this last step being accompanied by a pronounced change in colour of the polymer, which changes to dark orange.

After cooling to room temperature, the tape provided at the surface with its thin (thickness 5 to 10 μm) layer of polybenzoxazine thus formed was subsequently subjected to a conventional two-stage adhesive coating operation (two baths adhesive coating), first of all by immersion in a first aqueous bath (approximately 94% water) based on epoxy resin (polyglycerol polyglycidyl ether, approximately 1%) and on isocyanate compound (caprolactam-blocked isocyanate compound, approximately 5%), this first adhesive coating step being followed by drying (2 min at 100° C.) and then a heat treatment (5 min at 200° C.). The tape thus treated was then immersed in a second aqueous bath of RFL adhesive (approximately 81% by weight of water) based on resorcinol (approximately 2%), on formaldehyde (approximately 1%) and on a rubber latex (approximately 16% of NR, SBR and VP/SBR rubbers); finally, it was dried in an oven at 130° C. for 2 min and then heat treated at 200° C. for 5 min.

The brass tape thus coated with the polybenzoxazine film and then coated with adhesive was subsequently placed between two layers of conventional rubber composition for a belt reinforcement of a passenger vehicle tyre, this composition being based on natural rubber, on carbon black and silica as filler and on a vulcanization system (sulfur and sulfenamide accelerator); this composition was free of cobalt salt. The metal/rubber composite test specimen thus prepared was then placed under a press and the whole was cured (vulcanized) at 150° C. for 30 min under a pressure of 20 bar.

After vulcanization of the rubber, excellent adhesive bonding between the rubber matrix and the metal tape was obtained, despite the absence of cobalt salt in the rubber matrix; this is because, during peel tests (at 20° C.), it was found that the failure occurred systematically in the rubber matrix itself and not at the interphase between metal and rubber. Other adhesive bonding tests were performed on a bright (uncoated) steel tape; they also revealed excellent adhesion to the rubber (systematic failure in the rubber matrix).

In conclusion, the benzoxazine according to the invention allows the synthesis of polymers offering the metal reinforcers the major advantage of being able subsequently to be adhesively bonded to rubber matrices using simple textile adhesives, such as RFL adhesives, or else directly (that is to say, without employing such adhesives) to these rubber matrices, for example when the latter contain appropriate functionalized unsaturated elastomers, such as epoxidized elastomers. Thus, use may be made of metal reinforcers optionally coated with adhesive metal layers such as brass, and also surrounding rubber matrices free of metal salts, in particular of cobalt salts.

Moreover, this constituting a significant advantage compared to the other known polymers described in the introduction to the present document, the polybenzoxazines derived from benzoxazines of the invention have the noteworthy ability, at high temperature, to open their oxazine rings and to thus give a thermosetting polyphenolic resin structure. This gives them better heat stability. Finally, their specific microstructure makes it possible, very advantageously, to adjust the flexibility of the molecule according to the particular applications targeted.

The invention claimed is:

1. A sulfurized benzoxazine compound corresponding to formula (A):

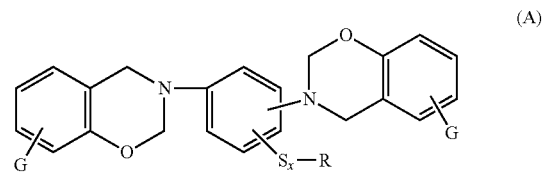

(A)

in which:
each benzene nucleus of the two oxazine rings bears at least one radical G;
the two oxazine rings are connected together via a central aromatic group, the benzene ring of which bears one, two, three or four groups of formula —$S_x$—R in which x is an integer from 1 to 8 and R represents hydrogen or a hydrocarbon-based group including 1 to 10 carbon atoms and optionally a heteroatom chosen from O, S, N and P; and
the at least two radicals G, which may be identical or different, are chosen from the group consisting of:
halogens;
groups —$OR_1$, —$SR_1$, and —$NR_2R_3$ in which $R_1$, $R_2$ and $R_3$, which may be identical or different, represent an alkyl containing 1 to 4 carbon atoms; and
aliphatic hydrocarbon-based groups including 1 to 8 carbon atoms, or cycloaliphatic hydrocarbon-based groups including 3 to 8 carbon atoms, or aromatic hydrocarbon-based groups including 6 to 12 carbon atoms, the hydrocarbon-based groups optionally including at least one heteroatom chosen from O, S, N and P.

2. The sulfurized benzoxazine compound according to claim 1, wherein the two nitrogen atoms of the two oxazine rings are, relative to each other, in the meta-position on the benzene ring which separates them.

3. The sulfurized benzoxazine compound according to claim 1, wherein the central benzene ring bears two groups of formula —$S_x$—R.

4. The sulfurized benzoxazine compound according to claim 3, wherein the two groups of formula —$S_x$—R are in the meta-position relative to each other on the central benzene ring.

5. The sulfurized benzoxazine compound according to claim 1, wherein x is within a range from 1 to 4.

6. The sulfurized benzoxazine compound according to claim 1, wherein R is an alkyl containing from 1 to 5 carbon atoms.

7. The sulfurized benzoxazine compound according to claim 6, wherein R is a methyl or an ethyl.

8. The sulfurized benzoxazine compound according to claim 5, wherein x is equal to 1 and R is a methyl.

9. The sulfurized benzoxazine compound according to claim 1, wherein each benzene nucleus of the two oxazine rings bears only one radical G.

10. The sulfurized benzoxazine compound according to claim 9, wherein the radical G borne by each benzene nucleus of the two oxazine rings is located in the para position relative to the oxygen of the oxazine ring.

11. The sulfurized benzoxazine compound according to claim 1, wherein the at least two radicals G, which may be identical or different, represent a halogen.

12. The sulfurized benzoxazine compound according to claim 11, wherein the halogen is bromine or chlorine.

13. A sulfurized benzoxazine compound corresponding to one of the formulae (A-7) or (A-7bis) below:

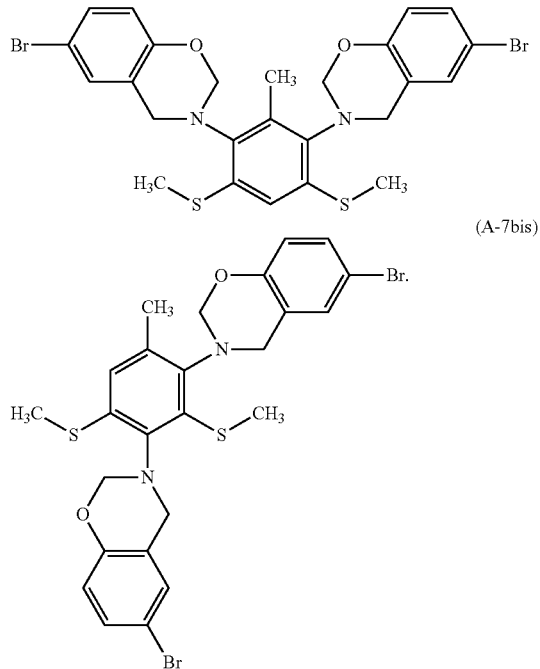

14. The sulfurized benzoxazine compound according to claim 1, wherein the at least two radicals G, which may be identical or different, represent a group chosen from —$OR_1$, —$SR_1$, and —$NR_2R_3$ in which $R_1$, $R_2$ and $R_3$, which may be identical or different, represent an alkyl containing 1 to 4 carbon atoms.

15. The sulfurized benzoxazine compound according to claim 1, wherein the at least two radicals G, which may be identical or different, represent an aliphatic hydrocarbon-based group including 1 to 8 carbon atoms, or a cycloaliphatic hydrocarbon-based group including 3 to 8 carbon atoms, or an aromatic hydrocarbon-based group including 6 to 12 carbon atoms, the hydrocarbon-based groups being able to optionally include at least one heteroatom chosen from O, S, N and P.

16. A sulfurized benzoxazine compound Corresponding to one of the formulae (A-5) or (A-5bis) below:

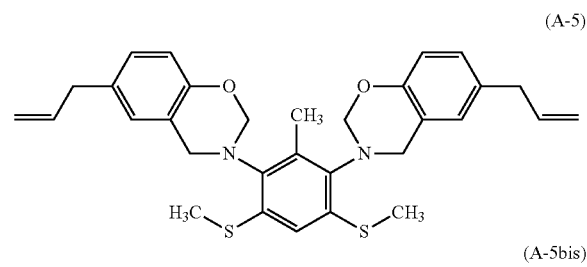

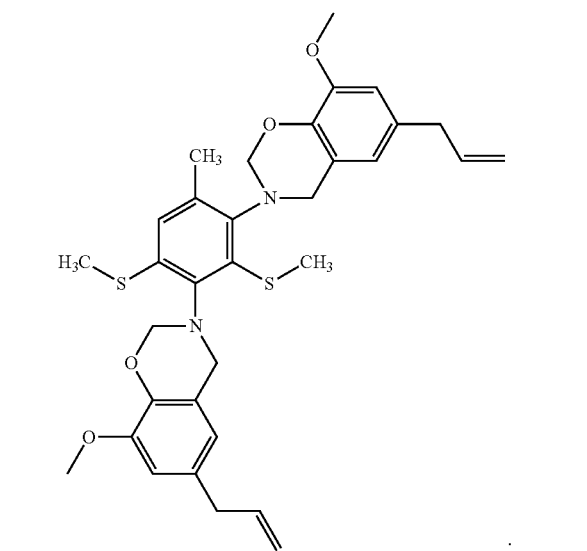

17. A process for synthesizing a polybenzoxazine comprising the step of:
polycondensating a sulfurized benzoxazine compound according to claim 1.

18. The process according to claim 17, wherein the sulfurized benzoxazine compound, as first monomer, is polycondensated with, as a second monomer, an aromatic diol or thiol compound.

19. The process according to claim 18, wherein the aromatic diol or thiol compound corresponds to formula (B):

(B) $HX_1$—$Ar_1$—Z—$Ar_2X_2H$ in which:

$X_1$ and $X_2$, which may be identical or different, represent O or S;

$Ar_1$ and $Ar_2$, which may be identical or different, represent an aromatic group; and Z represents O or $(S)_n$, n representing an integer greater than or equal to 1.

20. The process according to claim 19, wherein the aromatic diol or thiol compound corresponds to one of the formulae (B-1), (B-2) or (B-3) below:

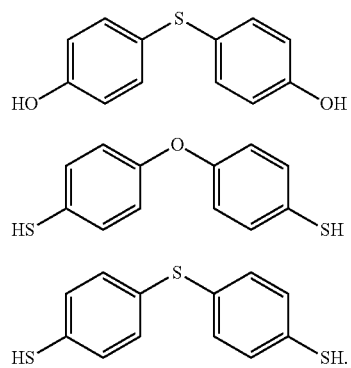
* * * * *